United States Patent [19]
Tajima

[11] Patent Number: 5,702,950
[45] Date of Patent: Dec. 30, 1997

[54] MAGNETIC MATERIAL ATTRACTING/ RELEASING CONTROL METHOD MAKING USE OF A PIPETTE DEVICE AND VARIOUS TYPES OF ANALYZER USING THE METHOD

[75] Inventor: Hideji Tajima, Tokyo, Japan

[73] Assignee: Precision System Science Co., Ltd., Tokyo, Japan

[21] Appl. No.: 462,434

[22] Filed: Jun. 5, 1995

[30] Foreign Application Priority Data

Jun. 15, 1994 [JP] Japan .................. 6-157959
Feb. 6, 1995 [JP] Japan .................. 7-039425

[51] Int. Cl.⁶ .............. G01N 35/10; G01N 33/543; B01L 3/02
[52] U.S. Cl. .............. 436/49; 436/43; 436/54; 436/174; 436/177; 436/180; 436/807; 422/63; 422/100; 422/101; 210/222; 210/695
[58] Field of Search .............. 436/43, 49, 47, 436/54, 174, 177, 180, 807, 809, 810; 422/63, 64, 65, 67, 100, 101; 210/695, 222, 223

[56] References Cited

U.S. PATENT DOCUMENTS

| | | | |
|---|---|---|---|
| 3,952,599 | 4/1976 | Ayres | 73/425.4 P |
| 3,985,649 | 10/1976 | Eddelman | 210/695 |
| 3,992,150 | 11/1976 | Retzer | 23/230 R |
| 4,195,526 | 4/1980 | Amos et al. | 73/425.6 |
| 4,275,591 | 6/1981 | Wand | 73/864.01 |
| 4,292,920 | 10/1981 | Smith et al. | 118/425 |
| 4,526,046 | 7/1985 | Oberli | 73/864.16 |
| 4,783,250 | 11/1988 | Pons et al. | 204/400 |
| 4,895,650 | 1/1990 | Wang | 210/222 |
| 4,988,618 | 1/1991 | Li et al. | 435/6 |
| 5,013,529 | 5/1991 | Itoh | 422/100 |
| 5,160,378 | 11/1992 | Tuunanen et al. | 134/25.1 |
| 5,171,537 | 12/1992 | Wainwright et al. | 422/100 |
| 5,183,638 | 2/1993 | Wakatake | 422/64 |
| 5,200,084 | 4/1993 | Liberti et al. | 210/695 |
| 5,200,151 | 4/1993 | Long | 422/100 |
| 5,344,610 | 9/1994 | Shaw | 422/100 |

FOREIGN PATENT DOCUMENTS

| | | |
|---|---|---|
| 0 638 809 A2 | 2/1995 | European Pat. Off. . |
| 2655426 | 6/1991 | France . |
| 2-151767 | 6/1990 | Japan . |
| WO95/00247 | 1/1995 | WIPO . |

Primary Examiner—Long V. Le
Attorney, Agent, or Firm—Lowe, Price, LeBlanc & Becker

[57] ABSTRACT

A magnetic material attracting/releasing control method makes use of a pipette device sucking a liquid from or discharging a liquid into a container. A magnet body or bodies are provided in a liquid suction line of the pipette device, and any magnetic material contained in liquid sucked into the liquid suction line by magnetic force are deposited on the internal surface of the line. The magnetic material is released and discharged together with liquid from the liquid suction line to a state where the effect of the magnetic force generated by the magnet body is cut off.

21 Claims, 9 Drawing Sheets

MAGNETIC MATERIAL ATTRACTING/RELEASING CONTROL METHOD MAKING USE OF A PIPETTE DEVICE AND VARIOUS TYPES OF ANALYZER USING THE METHOD

FIELD OF THE INVENTION

The present invention relates to a novel magnetic material attracting/releasing control method which can capture or diffuse a magnetic material. The invention also relates to various types of analyzer using the method.

It should be noted that, as defined in this specification, the "magnetic material" indicates not only to ball-like materials, but also to granular and corpuscular materials, and the form is not limited to a sphere; any form is allowable.

BACKGROUND OF THE INVENTION

In recent years, a variety of chemiluminescence methods (CL method) have been developed, which include, for instance, an enzyme immunoassay (EIA) that utilizes an antigen-antibody reaction, a chemiluminesence immunoassay (CLIA) in a narrow sense in which a chemical illuminescent compound is used for labeling as a tracer for immunoassay, and a chemilluminescent enzyme immunoassay (CLEIA) which detects enzyme activity with high sensitivity by using a chemical luminescent compound in a detection system.

As an inspection method using any of the techniques as described above, there have been known the magnetic particle method using magnetic particles each having a surface coated with an antigen or an antibody, the latex method using latex having a surface coated with an antigen or an antibody, the beads method using spheric beads each having a surface coated with an antigen or an antibody, or the so-called tube coating method using cells each having an inner wall coated with an antigen or an antibody. When taking into account efficiency of capturing an antigen or an antibody as well as production cost and running cost, However, methods using magnetic bodies such as magnetic particles or beads are far more advantageous.

In the conventional type of inspection methods using a magnetic material as described above, however, it is required to clean the magnetic material or have the magnetic material reacted to a reagent by gathering the magnetic material floating or depositing in a reactor, such as a specimen reaction container, or generating a floating state thereof several times in the reactor, however, it is extremely difficult to maintain high precision of gathering or agitating the magnetic material in the process, and this is one of the reasons why the inspection method making use of magnetic material has not been automatized for various applications.

Description is made of a flow in an immuno chemical process making use of a magnetic material as described above with reference to FIG. 9. In this flow, at first when a required quantity of specimen is sampled in a container 1 with a first pipette device $P_1$ in step (a), a reaction insoluble magnetic liquid 3 is poured into the container 1 by a second pipette device $P_2$ in step (b). Agitation by a vibrating agitator is executed in step (c), incubation (under a constant temperature) is executed in step (d), and attraction of magnetic material by a magnet M and discharge of the liquid are executed in step (e). A cleaning liquid is then poured by a third pipette device $P_3$ into the container in step (f).

Then in step (g), agitation is carried out by an shaking agitator, in step (h), the magnetic material 2 is attracted by the magnet M with the cleaning liquid discharged, in step labeling liquid 6 is poured in through a fourth pipette device $P_4$, in step (j) agitation is carried out by a shaking agitator, in step (k) incubation (reason under a constant reaction) is carried out, then in step (l) the magnetic material is attracted by the magnet M With the reaction liquid discharged, in step (m) the cleaning liquid is poured in through a fifth pipette device $P_5$. Then, in step (n), agitation is carried out by the shaking agitator.

Then, for instance, in CLEIA method, in step (o) the magnetic material 2 is attracted by the magnet M with the cleaning liquid discharged, in step (p) the carried liquid is poured in, in step (q) agitation is carried out by a shaking agitator, and then in step (r) the sample is left for a certain period of time, and in step (s) the quantity of light emitted from the reaction system is measured with an optical measuring instrument such as PMT.

On the other hand, in case of CLIEA method, after step (n) described above, in step (t) a cleaning liquid containing the magnetic material 2 in the vessel 1 is sucked out with the cleaning liquid poured into a measuring cell with a filter provided thereon, and the magnetic material 2 contained in the cleaning liquid is collected by the filter. Then, in step (u), hydrogen peroxide liquid ($H_2O_2$) is poured into the magnetic material 2 collected by said filter to have liquid emitted transitionally, and a quantity of emitted light is measured by PMT tightly protected against light coming from outside.

On the other hand, in a checking method, like the CLEIA method or EIA method, in which light emission is continued for a certain period of time after a substrate liquid is poured in step (s), in step (t) a quantity of light generated in the reaction is measured with an optical measurement instrument such as a PMT.

The above description relates to the conventional type of inspection method using a magnetic material, but as clearly understood from the foregoing, in the conventional inspection method making use of the type of magnetic material as described above, it is required to attract the magnetic material onto the internal wall of a container and then homogeneously diffuse the attracted magnetic material into a liquid several times. It is extremely difficult to execute separation of the magnetic material from a liquid, agitation, and cleaning the container at high precision, a problem to be solved.

Namely, when separating the magnetic material from a liquid, in the conventional type of inspection method, generally magnetic attraction is produced on a side wall of a large container, requiring a long time to attract any magnetic material diffused in a liquid onto the internal wall of the container. Efficiency in gathering the magnetic material thus is disadvantageously very low.

Also, when gathering magnetic material on the internal surface of a container and inserting a pipette into a liquid to absorb the liquid, the magnetic material may be absorbed together with the liquid, and it is extremely difficult to completely capture the magnetic material.

Furthermore, when agitating the liquid with magnetic material diffused therein, generally to eliminate magnetism in a magnet and mix and diffuse the magnetic material once absorbed in liquid in the container, vibration is usually employed. However, it is difficult to diffuse the magnetic material in the liquid homogeneously, and the liquid containing the magnetic material mixed therein sometimes splashes out onto an upper surface of the container, another problem to be solved. As a result, with vibration as employed agitation in the conventional technology, a washing off the liquid containing magnetic material splashed out onto the upper surface of the container is required. Hence, processing becomes more complicated, and if this operation for washing off the liquid is carried out incompletely, the subsequent steps in the process are seriously affected.

Furthermore, when cleaning the liquid and magnetic material in the container as described above, materials other than those deposited on the surface of the magnetic material are removed by carring out processes for separating as well as agitating as described above, but the same problems as those that arise in separating and agitating may occur.

Also, in the inspection method making use of the conventional type of magnetic material, if a reaction process or a treatment process is a very specific one, it is required to build mechanisms for separation, agitation, and cleaning as well as a control system suited to the specific process. Hence, the mechanisms or the control system become very complicated, and it is practically impossible to carry out an inspection making use of a magnetic material based on a very specific reaction or treatment process. As a result, the facility or the operating cost becomes very high.

In addition, in the method of gathering magnetic material based on the aforementioned conventional technology, it is difficult to position the magnet as described above in such a container as, for instance, a microplate, and even if possible, it is difficult to position a magnet on a side face of the container. It is also difficult to carry out separation by attracting the magnetic material from a liquid, agitation and cleaning, and as a result it is extremely difficult to downsize the container by using a microplate, a fatal disadvantage.

SUMMARY OF THE INVENTION

It is an object of the present invention to provide a magnetic material attracting/releasing control method using a novel pipette, the most remarkable feature of which consists in that capturing and gathering magnetic material diffused in a liquid from the liquid is not executed on the side of a container in which a specimen is accommodated but in a pipette which can absorb and discharge the liquid containing the magnetic material. The pipette can realize substantial improvement of measurement precision in an inspection method making use of this type of magnetic material by for complete attraction in a short period with magnetism of a magnet provided on the absorption/discharge side of a pipette chip or the like in this pipette device. Cross-contamination is prevented if a disposable pipette chip is used, and the method can easily respond to various types of inspection each based on a specific reaction or treatment process, respectively. An inspection device using a magnetic material can be produced material with the invention, simple in terms of construction and operation thereof and also more versatile and low in cost.

To achieve the objects as described above, in a magnetic material attracting/releasing control method making use of a pipette according to the present invention, a magnet is provided in a liquid suction line in a pipette for sucking and discharging a liquid from inside a container. Any magnetic material in a liquid attracted by the liquid suction line due to magnetism in the magnet is absorbed and maintained on the internal surface of the liquid suction line, and then the magnetic material is separated from the liquid suction line and discharged together with the liquid from the liquid suction line.

In the present invention, to enhance processing capability, a plurality of liquid suction lines are provided in parallel to each other. Sucking or discharging a liquid in each liquid suction line is driven and controlled so that absorption or separation of magnetic material in the liquid will be executed concurrently. This enables realization of a multi-channel system allowing concurrent processing of a plurality of specimens.

Furthermore, in the present invention, to enhance the processing capability and respond to any liquid requiring a specific treatment process, it is possible to provide a plurality of liquid suction lines described above. Each liquid suction line is controlled independently at a different timing so that suction and discharge of liquid are controlled to attract or separate the magnetic material mixed and diffused therein through a specific treatment process, respectively.

In the present invention, only at least one liquid suction line as described above is required. Improvement in processing capability can be achieved only by integrating a liquid suction line and magnetic material into a unit and providing a plurality of units as described above along a container transfer line.

Also, in the present invention, the magnet described above includes any type of permanent magnet or electric magnet as far as it can generate magnetism for attracting a magnetic material, and one or more pieces of magnet can be provided in each liquid suction line in correspondence to the diameter of the liquid suction line, quantity of magnetic material to be attracted, and size thereof. Various types of mode for locating the magnets can be considered, for instance, magnets may be located in the direction in which a liquid flows in the liquid suction line or at opposite positions in both sides of the liquid suction line, or in the radial direction.

Furthermore, in the present invention, the above magnets can be located in the outside of the liquid suction line, or directly onto the liquid suction line.

When locating magnets outside the liquid suction line as described above, by using a plurality pieces of permanent magnet as the magnet bodies above and locating the magnet bodies on or near the liquid suction line, it is possible to absorb and maintain magnetic material contained in liquid attracted to the liquid suction line onto the internal surface of the liquid suction line. It is further possible to discharge the magnetic material together with the liquid from the liquid suction line by moving the magnetic bodies away from the liquid suction line to separate the magnetic material from the line.

When directly locating the magnet bodies on or near the liquid suction line, by forming the magnet bodies with electro-magnets and generating magnetism in the electro-magnets, it is possible to absorb and maintain magnetic material contained in liquid sucked into the liquid suction line on an internal surface of the liquid suction line. It is also possible to separate the magnetic material from the liquid suction line by providing controls over the electro-magnets so that the magnetism disappears or is reduced for discharging the magnetic material together with the liquid from the liquid suction line. It is needless to say that, for forming the electro-magnet as described above, an exciting coil may directly be attached to the liquid suction line itself or the coil may be wound around the liquid suction line. A configuration is also allowable in which the electro-magnet can be moved closer to or away from the liquid suction line.

As an important feature of the present invention, a liquid suction line is formed by dismountably mounting a pipette chip onto a tip section of the liquid sucking side thereof. The magnet body is arranged so that magnetism generated by the magnet body works over magnetic material inside the pipette chip.

Thus by making it possible, when sucking or discharging a liquid containing magnetic material with a pipette chip, to absorb the magnetic material obtained in the liquid onto an internal surface of the pipette chip, the magnetic material can be captured as completely as possible. It is also possible to transfer a pipette chip with magnetic material deposited on an internal surface thereof, as is, to a next reaction or treatment step. This can not be realized without using the pipette device according to the present invention, and at least in that sense the present invention is novel.

The pipette chip described above is used repeatedly only for the same specimen in a process in which the specimen is processed according to a specified processing sequence for inspection to prevent cross-contamination. Any number of pipette chips may be used for the same specimen according to the requirement for a reaction or a treatment process in various types of inspection.

Also, in the present invention, if the liquid suction line is formed with a nozzle system in which a pipette chip can not be loaded or unloaded, it is possible to separate the magnetic material from the liquid, agitate and clean the internal as well as external surface of the liquid-contacting section contacting liquid in the liquid suction line by means of sucking or discharging the liquid to a degree where cross-contamination will not occur.

Another feature of the present invention consists in that separation of the magnetic material from the liquid, agitation and cleaning can be carried out by sucking liquid into or discharging a liquid from the liquid suction line once or more than once.

Namely, in the present invention, separation of magnetic material from a liquid is executed by maintaining the state where magnetic material is absorbed and deposited on the internal surface of a liquid suction line and discharging only the liquid. This is alternatively accomplished by inserting a pipette chip with magnetic material attracted by a magnet body and deposited on an internal surface thereof into liquid stored in an other container and repetitiously sucking and discharging the liquid to a state where the magnetic material is not affected by magnetism in the magnet body described above.

Thus, by executing separation between a liquid and magnetic material contained in the liquid by means of repetitiously for sucking and discharging the liquid in a liquid suction line of a pipette device, it is possible to almost completely capture the magnetic material. The almost complete separation of magnetic material from a liquid containing the magnetic material can be realized in all processes requiring separation of magnetic material from a liquid containing it.

Also, in the present invention, when a pipette chip is mounted on a liquid suction line, the agitation and cleaning steps described above are executed by transferring the pipette chip with magnetic material attracted by the magnet body and deposited onto an internal surface thereof as is to the position for agitation and cleaning and then repeating the operations for sucking and discharging the liquid. In this case, agitation and cleaning can be executed with the magnetic material deposited on an internal surface of a pipette chip or executing an operation for sucking and discharging the liquid once or more to a state where the magnetic material is not affected by a magnet body.

As described above, with the present invention, it is possible to homogeneously diffuse magnetic material in a liquid by sucking and discharging the liquid in a liquid suction line in a pipette device. It is also possible to improve the cleaning efficiency, and in addition, although liquid sucking and discharging is executed between a liquid suction line and a container, the liquid containing magnetic material does not splash out from the container. Hence, the agitation and cleaning processes can be executed under stable conditions without causing the possibility of lowering precision in measurement due to splashing of the liquid containing magnetic material.

It should be noted that, in the present invention, the operations for separating magnetic material from a liquid containing it therein, agitation and cleaning can be executed by transferring a magnet body to a liquid containing magnetic material previously stored in a liquid storage section in a cartridge having a plurality of liquid storage sections therein. Sucking or discharging the liquid is performed according to need, or by maintaining the state where magnetic material is deposited on an internal surface of a pipette chip and discharging the residual liquid from the container. Then, liquid required for the next process is poured into the same container and sucking or discharging the liquid poured anew is carried out with the pipette chip. In brief, in the present invention, any specific form of a container is not required for sucking and discharging liquid in a liquid suction line to execute the operations for separating magnetic material from a liquid containing it therein, agitation, and cleaning.

Another significant feature of the present invention is that it is possible to execute both qualitative and quantitative assessment of a target material contained in a liquid by accurately controlling the quantity of liquid sucked by a liquid suction line.

The method according to the present invention is applicable to and effective in a reaction generated between magnetic material and a liquid not containing any magnetic material, a material present in a liquid, and other materials which can physically and chemically be deposited on a magnet body. The materials include immunological materials, biological materials, and molecular-biological materials such as antigens, antibodies, proteins, enzymes, DNA, vector DNAs, RNAs or plasmid. The method can be applied to inspection or a analyzer for isotopes required for qualitative or quantitative analysis, enzymes, and other labeling materials used for chemiluminescence, fluoro-illuminescence, and electro-chemical illuminescence or the like. For instance, the method according to the present invention can be applied to apparatus for immunological assay, inspections making use of chemical reaction, extraction, recovery and separation of DNAs.

For instance, if the method according to the present invention is applied to an immunochemical inspection apparatus, a container is formed in a cassette having a plurality of liquid storage sections. A liquid or reagent required for reaction or processing is poured into each liquid storage section, and the container should preferably be transferred with a magnetic material attracted by the magnet body to and deposited on an internal surface of a liquid suction line as is. In this case, the liquid is previously poured into each liquid storage section as described above, and only a portion thereof may be processed or be processed gradually in the treatment process.

Furthermore, a specimen can directly be measured quantitatively, for instance, in a parent specimen container and then poured into each liquid storage section. It should be noted that the liquid storage sections in the cassette may be arranged either in a single array or in a plurality of arrays and formed into a form like a microplate. If the cassette is a form like a microplate, a multi-channel system can be realized by locating a plurality of liquid suction lines in correspondence to the liquid storage section arrays, and thus the processing capability is substantially improved.

Other objects and features of this invention will become understood from the following description with reference to the accompanying drawings.

DESCRIPTION OF THE PREFERRED EMBODIMENTS

Detailed description is made for a case where the present invention is applied to an immunochemical inspection method based on the chemilluminescence method with reference to an embodiment of the present invention shown in the attached drawings. As described above, the field of application of the present invention is not limited to the embodiment, and the present invention can be applied to any case as far as a magnetic material attracting/releasing method making use of a pipette device is applied and magnetic material is used.

Figure 1:
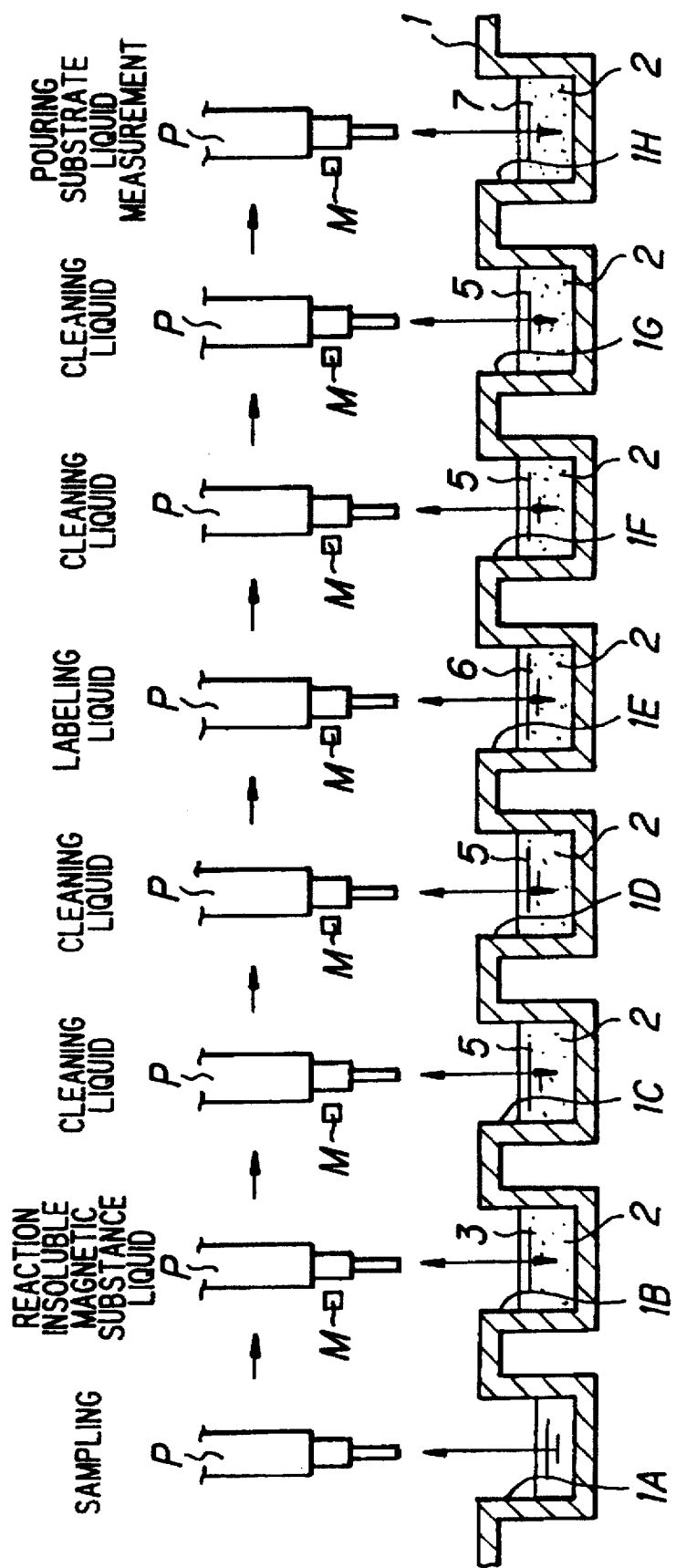
FIG. 1 is a flow chart showing processes in a case where the present invention is applied to an immunochemical inspection method based on the chemiluminescence method.

A flow of an immunochemical inspection according to the present invention as compared to a flow of the conventional type of immunochemical inspection is described below with reference to FIG. 1.

It should be noted that, in this embodiment, the magnetic material is defined as magnetic material, which can be adhered to a surface of an antigen or an antigen, being attracted by a magnet body for B/F separation (separation of materials bound to antigen or antibody and those not bound to them).

In this figure, the sign P indicates a pipette chip for pouring a specified quantity of specimen from a parent vessel, such as a blood tube (not shown), into a specimen reaction container 1 and also for discharging from or sucking into the specimen reaction container 1 a reaction insoluble magnetic material liquid 3, a cleaning liquid 5, an enzyme-labeling liquid 6, a substrate liquid 7, a reaction stop liquid 8 or the like.

Figure 2:
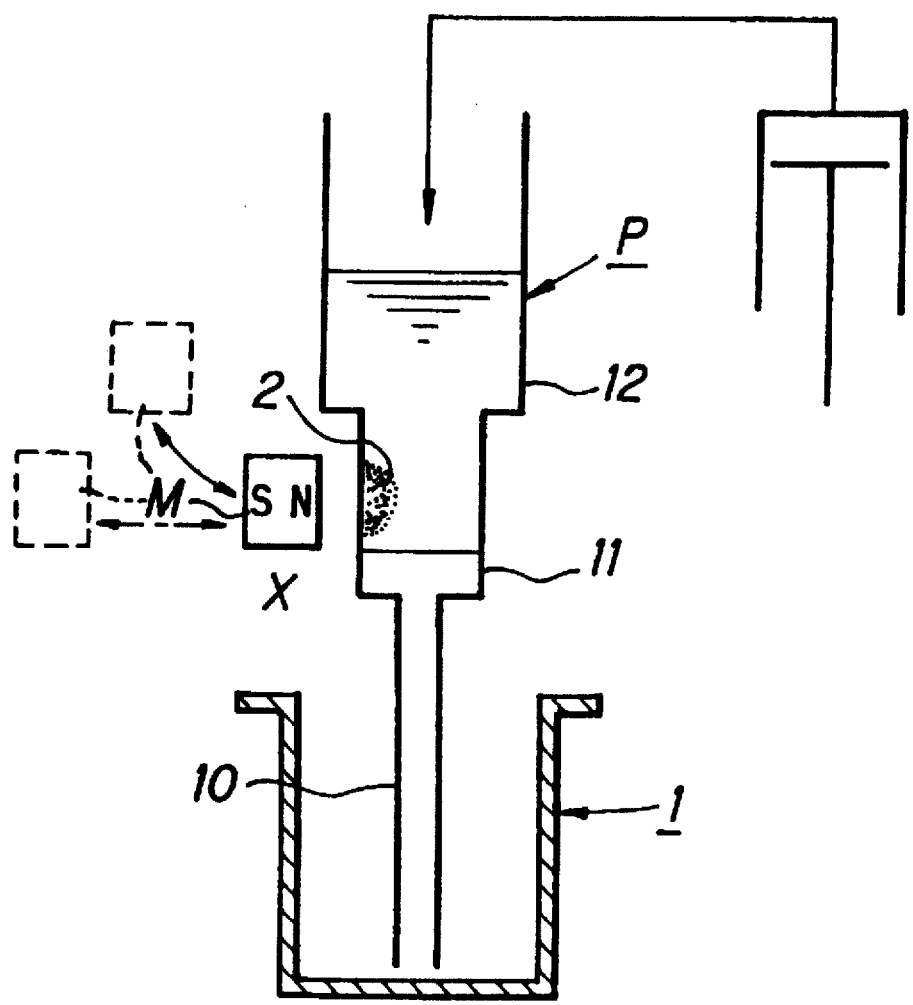
FIG. 2 is a cross-sectional view showing an example of a pipette chip used in the present invention.

As shown in FIG. 2, the pipette chip P has a three-staged form consisting of a thinnest section 10 inserted into the specimen reaction container 1, a medium diameter section 11 having a larger diameter than the thinnest section 10, and a large diameter section 12 having a larger diameter than the medium diameter section 11. A magnet M for attracting the reaction insoluble magnetic material 3 is detachably fitted to an external peripheral surface of the medium diameter section 11 with a mechanism for sucking or discharging liquid in a cylinder or the like disconnectably connected and communicated to a top edge section of this pipette chip P. It is needless to say that the form of this pipette chip P is not limited to that shown in this figure; any form is allowable on the condition that, when a liquid is sucked into the pipette chip P, any magnetic material contained in the liquid is captured by the magnet M without fail. To completely capture the magnetic material with the magnet, however, it is desirable to form the section contacted by the magnet with a small diameter. This also is preferable for efficiently controlling flow rate while sucking or discharging liquid.

It should be noted that, when extracting, recovering, or separating DNAs, a molded pipette chip having a large diameter may be used to prevent the DNAs from being broken or damaged due to physical force effecting magnetic material deposited on the DNAs and generated when liquid is sucked or discharged.

In the specimen reaction container 1, a plurality of liquid storage sections 1A through 1H are provided in a straight array, in a loop, or in a zig-zag form with a roughly specified quantity of specimen having been poured in the liquid storage section 1A, a specified quantity of reaction insoluble magnetic material liquid 3 in the liquid storage section 1B, a specified quantity of cleaning liquid 5 in the liquid storage sections 1C and 1D, a specified quantity of labeling liquid in the liquid storage section 1E, a specified quantity of cleaning liquid 5 in the liquid storage sections 1F and 1G, each filled with the liquid before start of inspection, and a substrate liquid in the liquid storage section 1H for measurement of the light-emitting state.

In the case of the CLIA or CLEIA inspection, the specimen reaction container 1 is made of opaque material to prevent any effect by illuminescence, and in the case of the EIA inspection at least the bottom section is made of a transparent material.

When carrying out immunochemical inspection according to the present invention using the specimen reaction container 1 constructed as described above and the pipette chip P, the specimen having been poured into the liquid storage section 1A by a roughly specified quantity is sucked with the pipette chip P above by a specified quantity for quantitative analysis.

Then, the pipette chip P with the specimen sucked thereinto is transferred and all of the specimen having been sucked is discharged into the reaction insoluble magnetic material liquid 3 in the liquid storage section 1B. A mixture of the specimen and the reaction insoluble magnetic material liquid 3 then is repeatedly sucked and discharged with the pipette chip P (this operation is called liquid sucking/discharge hereinafter) to generate a state where the magnetic material 2 has been homogeneously agitated and mixed therein. In several hours, all, or a specified quantity of, the incubated mixed liquid is sucked with the pipette chip P.

In this step, the magnetic material 2 floating in the mixed liquid sucked by the pipette chip P is captured onto an internal wall surface of the medium diameter section 11 due to magnetism of the magnet M provided outside the pipette chip P, as shown in FIG. 2, when the mixed liquid passes through the medium diameter section 11 of the pipette chip P. The mixed liquid is sucked into the pipette chip P to the height shown in FIG. 2, so that, when all the mixed liquid is sucked into the pipette chip, the bottom face x comes near a lower edge of the magnet M or to a level higher than that and the magnetic material 2 is completely captured.

After all the magnetic material 2 has been captured, the mixed liquid with the magnetic material having been removed therefrom is discharged into the liquid storage section 1B, and only the magnetic material 2 remains in the pipette chip P. As the magnetic material 2 is wet then, even if the mixed liquid is exhausted, the magnetic material 2 is kept deposited on an internal surface of the medium diameter section 11 of the pipette chip P, so that, even if the pipette chip is transferred, the magnetic material rarely drops off from the internal surface. Then the pipette chip P is transferred to the next liquid storage section 1C with the magnetic material 2 captured therein, and sucks the cleaning liquid 5 in the liquid storage section 1C. Then the magnet M moves away from the pipette chip P to release the magnetic material 2, and therefore by sucking and discharging the cleaning liquid 5, all the magnetic material 2 can efficiently be cleaned.

After the operations for sucking and discharging the liquid are finished, the pipette chip P slowly sucks all the cleaning liquid 5 (for 5 to 10 seconds) in the liquid storage section 1C. Then the magnet M is again moved toward the pipette chip P to capture all the magnetic material 2 floating in the sucked cleaning liquid 5, and the cleaning liquid 5 with the magnetic material 2 having been removed therefrom is discharged into the liquid storage section 1C, so that only the magnetic material 2 remains in the pipette chip P.

Then the pipette chip P is transferred to the next liquid storage section 1D with the magnetic material 2 captured therein and sucks the cleaning liquid 5 in the liquid storage section 1D, where the operations for cleaning and capturing the magnetic material 2 are executed according to the same sequence as that in the liquid storage section 1C.

Then the pipette chip P is transferred to the next storage section 1E with the cleaned magnetic material 2 captured therein, and sucks the labeling liquid 6 in the liquid storage section 1E. Then the magnet M moves away from the pipette chip P to release the magnetic material 2, and thus by sucking and discharging the labeling liquid 6, all the magnetic material 2 and the labeling liquid 6 can be reacted to each other homogeneously.

After the operations for sucking and discharging the liquid are finished, incubation is continued for a specified period of time, and then the pipette chip P slowly sucks all the labeling liquid 6 in the liquid storage section 1E (for instance, for 5 to 10 seconds). Then the magnet M again goes near the pipette chip P to capture all the magnetic material 2 floating in the sucked labeling liquid 6, and the labeling liquid 6 with the magnetic material 2 having been removed therefrom is discharged into the liquid storage section 1E, and only the magnetic material 2 remains in the pipette chip P.

Then the pipette chip P is transferred to the next liquid storage section 1F with the magnetic material 2 captured therein, sucks the cleaning liquid 5 in the liquid storage section 1F, executes operations for cleaning and capturing the magnetic material 2 according to the same sequence as those in the liquid storage sections 1C and 1D, sucks the cleaning liquid 5 in the liquid storage section 1G according to the same sequence as that for sucking the cleaning liquid in the liquid storage section 1F, and then executes operations for cleaning and capturing the magnetic material 2.

Then the pipette chip P is transferred to the liquid storage section 1H, and for instance if a measurement in which illuminescence is continued after mixed with a substrate liquid and a certain period of time is required until a rate of light emission is stabilized as in the CLEIA inspection is to be carried out, the substrate liquid 7 previously stored in the liquid storage section 1H is sucked by the pipette chip P. Then the magnet M moves away from the pipette chip P and releases the magnetic material 2, so that it is possible to homogenize the reaction between the magnetic material 2 and the substrate liquid 7 by sucking and discharging the substrate liquid 7.

Figure 3:
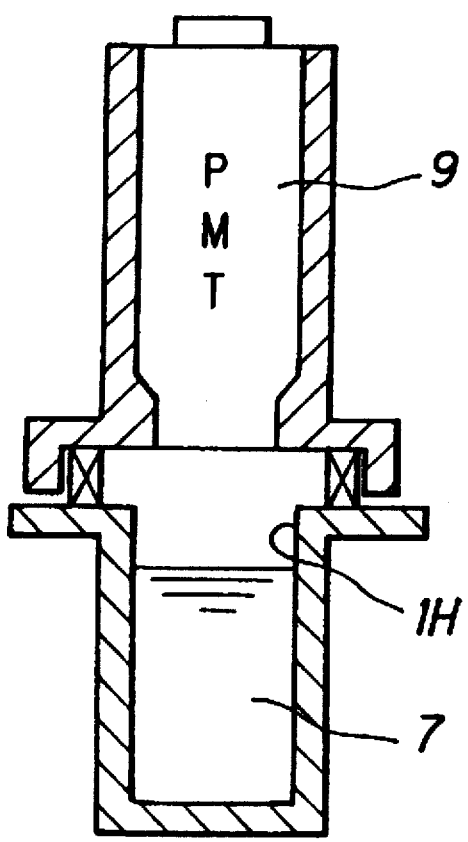
FIG. 3 is an explanatory view showing an example of the general configuration of a measurement section in a case where the present invention is applied to an immunochemical inspection method based on the CLEIA method.

When the operations for sucking and discharging the liquid have been finished and incubation has been executed for a certain period of time, a quantity of emitted light is measured by the optical measurement instrument 9 such as a PMT as shown in FIG. 3.

Figure 4:
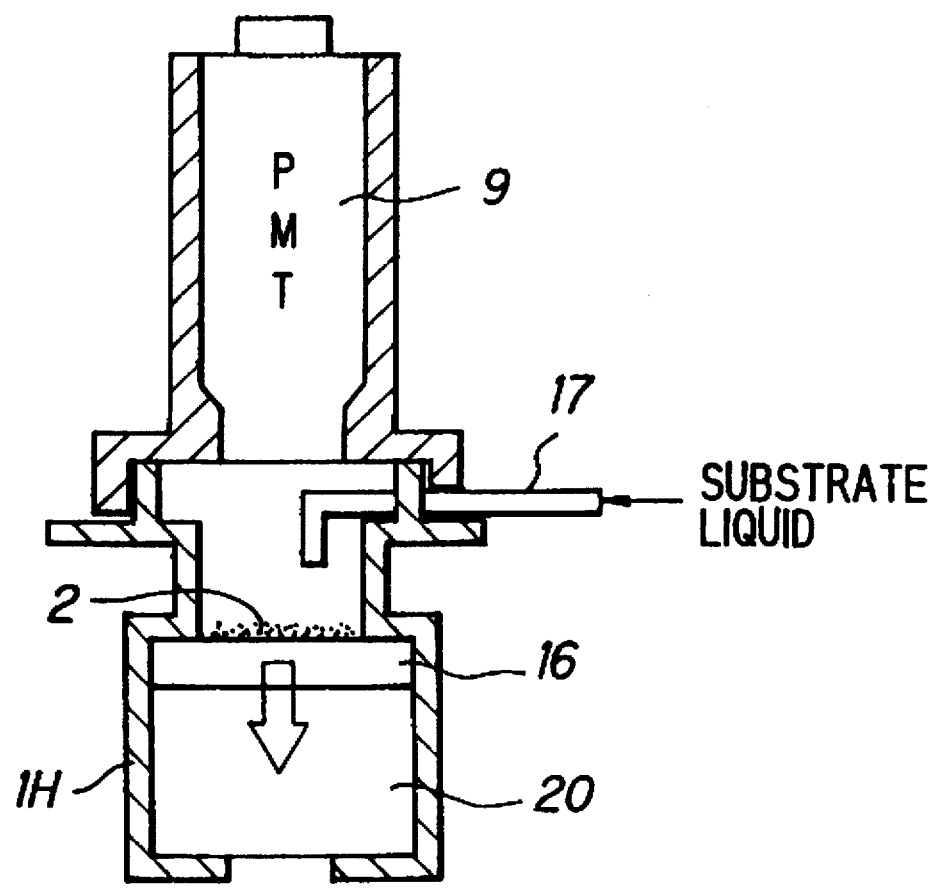
FIG. 4 is an explanatory view showing an example of the general configuration of a measurement section in a case where the present invention is applied to an immunochemical inspection method based on the CLIA method.

In the case of an inspection method in which illuminescence is continued only for a very short period of time as in CLIA inspection, the liquid storage section 1H is provided as shown in FIG. 4, a filter 16 and a water-absorbing pad 20 is provided in the liquid storage section 1H, and the magnetic material 2 is discharged together with the cleaning liquid 5 sucked in the previous process from the pipette chip P into the liquid storage section 1H to have the magnetic material 2 captured by the filter 16. Then a light-emitting trigger liquid 7 such as hydrogen peroxide liquid ($H_2O_2$) is supplied from a nozzle 17 to make the magnetic material emit light, and a quantity of light emitted when said substrate liquid is poured may be measured with an optical measurement instrument 9 such as a PMT.

Figure 5:
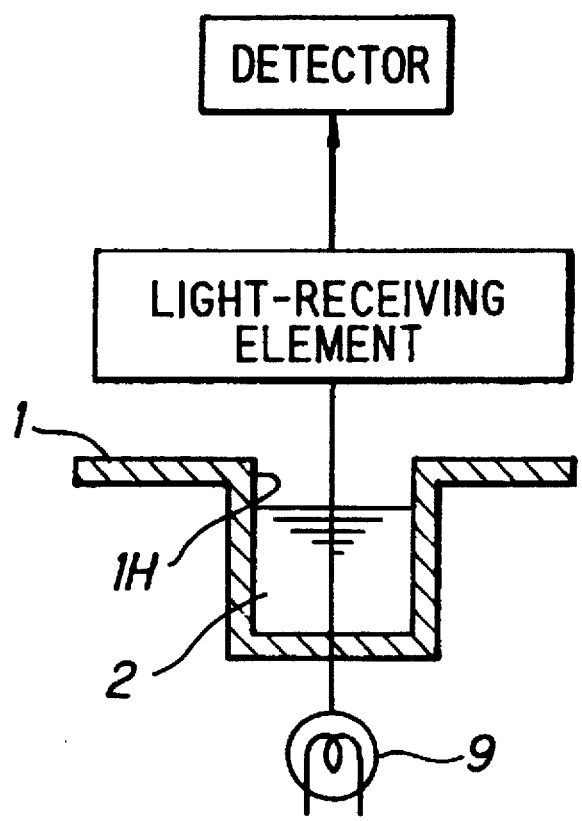
FIG. 5 is an explanatory view showing an example of general configuration of a measurement section in a case where the present invention is applied to an immunochemical inspection method based on the EIA method.

Furthermore, in the case of EIA inspection, after the substrate liquid 7 is poured, a reaction stop liquid is supplied and as shown in FIG. 5, a light beam having a specified wavelength is irradiated from a bottom section of the liquid storage section 1H, and a degree of absorbency is measured by a light-receiving element and a detector by checking the specific color.

Thus, with the specimen reaction container 1 according to the present embodiment, it is possible to respond to a plurality of types of immunochemical inspection by changing only configuration of the liquid storage section 1H in correspondence to various inspection methods, so that the versatility can substantially be improved. Also a multi-channel system of this type can be realized by providing liquid storage section in a plurality of arrays in the specimen reaction container 1 to form it into a form like a microplate.

Then the pipette chip P and the specimen reaction container 1 are disposed.

It should be noted that, although description of the embodiment above assumed a case in which the specimen reaction container 1 is cleaned twice after the reaction insoluble magnetic material liquid 3 is discharged and furthermore 2 times after the labeling liquid 6 is discharged, the present invention is not limited to the configuration described above: the specimen reaction container 1 may be cleaned any number of times according to need.

Also the above description assumes the configuration in which the pipette chip P is transferred to each liquid storage section in the specimen reaction container 1, but a configuration is allowable in which the pipette chip P is moved only in the vertical direction and the specimen reaction container 1 is intermittently transferred for executing each of the operations described above.

Furthermore, the description of the above embodiment assumed a case where the pipette chip P and the specimen reaction container 1 are disposable, although a configuration is allowable where the pipette chip P and the specimen reaction container 1 can be cleaned and used repeatedly. Also, the description of the above embodiment assumed a case in which the waste liquid after being sucked by the pipette chip P is recycled to the original liquid storage section from which the liquid was sucked. A configuration is also allowable, however, where the waste liquid is returned to a waste liquid section provided outside the specimen reaction container 1.

Figure 6:
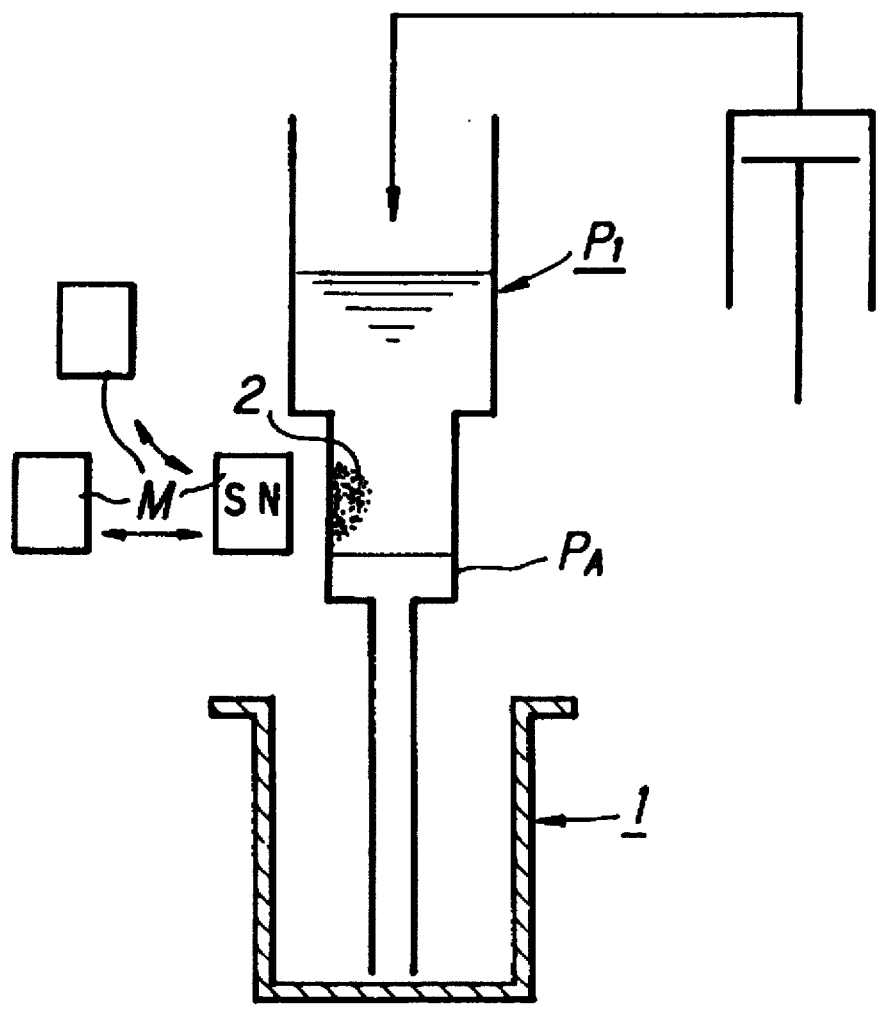
FIG. 6 is an explanatory view showing an example of the arrangement of a magnet in a case where a liquid suction line in the present invention is a nozzle system.

It is needless to say that the present invention is applicable to a case where the pipette chip P is not used and a liquid suction line is formed as a nozzle system, and in this case, the configuration as shown in FIG. 6 is allowable where a lower edge section $P_A$ of the liquid suction line $P_1$ is formed into a thin diameter section, and the magnet M or an electro-magnet is moved to or away from the lower edge section $P_A$ of the liquid suction line $P_1$. When using the electro-magnet, a configuration is allowable where the electro-magnet is fitted to the thin diameter section of a liquid suction line or the electro-magnet is directly wound around the thin diameter section of the liquid suction line and operations for separating magnetic material from a liquid, agitation, and cleaning are executed by turning ON or OFF a current.

Figure 7:
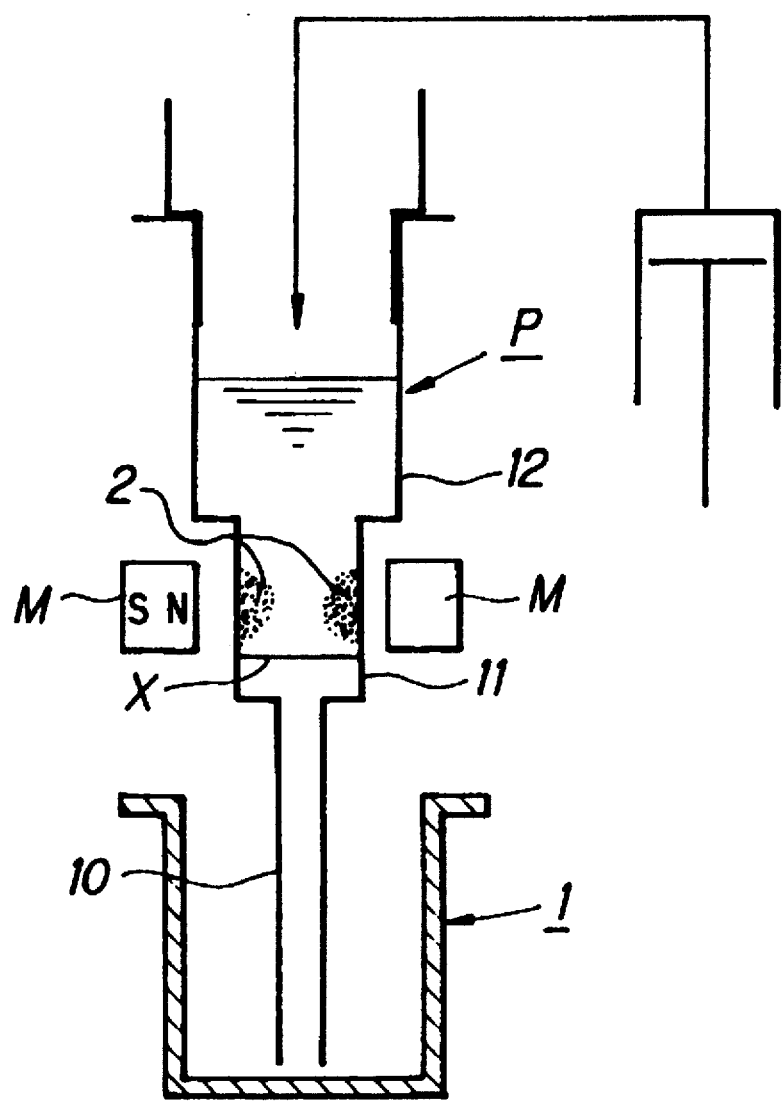
FIG. 7 is an explanatory view showing another example of an arrangement of a magnet in the present invention.
Figure 8:
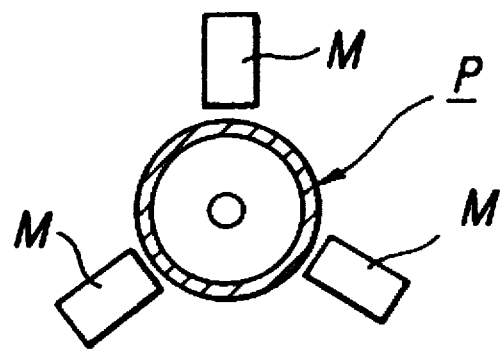
FIG. 8 is an explanatory view showing still another example of an arrangement of a magnet in the present invention.
Figure 9:
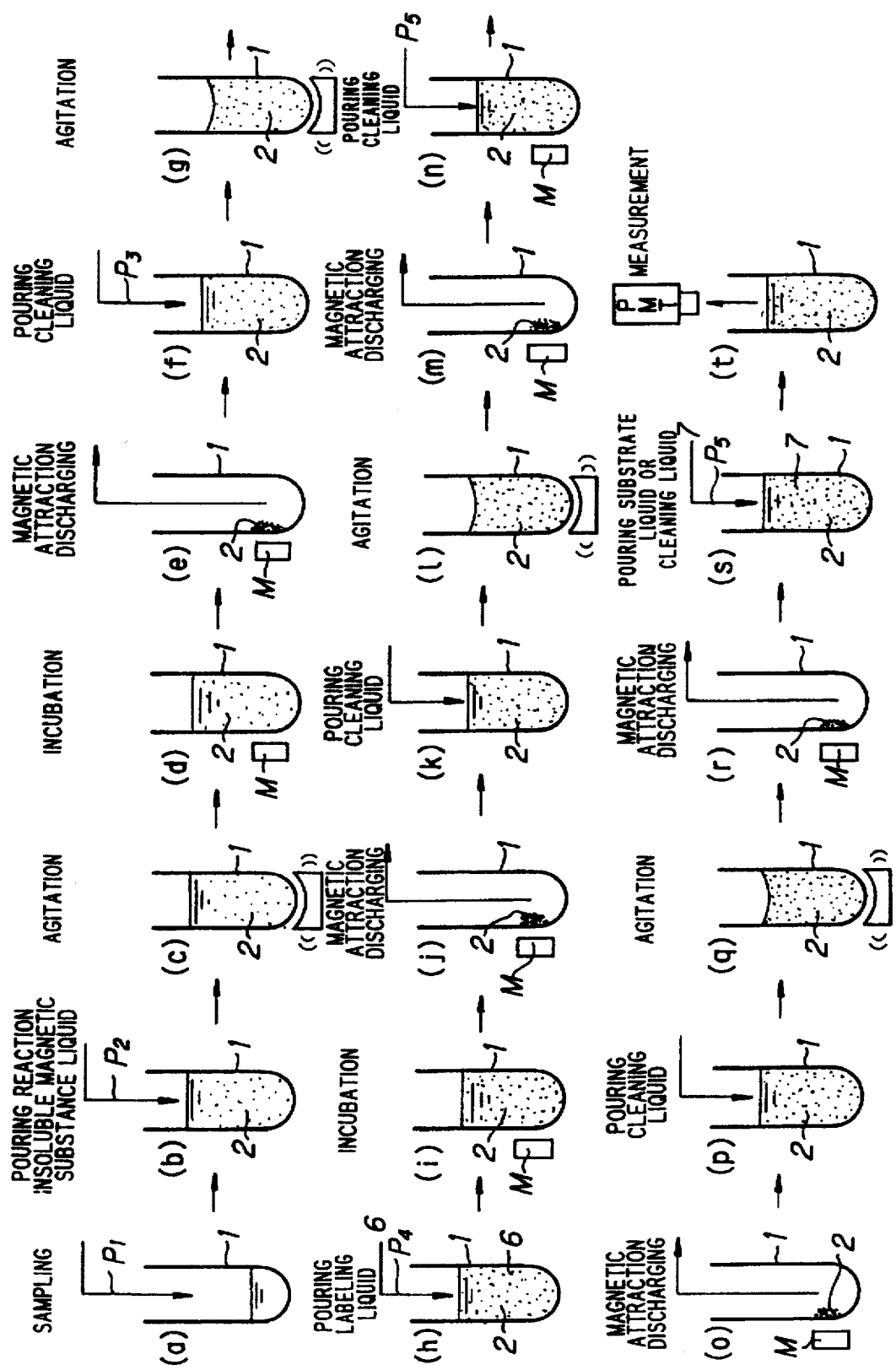
FIG. 9 is a flow chart showing processes in an immunochemical inspection method based on the conventional type of chemiluminescence method.

Also, the description of the embodiment above assumes a case where the magnet M is detachably fitted to one side of the medium diameter section 11 of the pipette chip P, but the magnets M may be provided in both sides of the medium diameter section 11 as shown in FIG. 7. Also, a plurality of magnets M may be provided in a radial form around the medium diameter section 11 shown in FIG. 8, and also a plurality of magnets may be provided along the longitudinal direction of the medium diameter section 11, although that case is not shown herein.

As described above, in the present invention, magnetic material is loaded or unloaded by making use of a pipette device, and capture of the magnetic material is executed not in the side of a container in which a liquid is stored, but in the side of a liquid suction line for sucking and discharging a liquid containing magnetic material by making use of magnetism in a magnet provided therein, so that the magnetic material can almost completely be captured within a short period of time.

Also, in the present invention, a multi-channel system in which a plurality of specimens can be processed concurrently and the processing capability can be enhanced by providing a plurality of the liquid suction line described above and controlling the operations for sucking and discharging a liquid so that each liquid suction line absorbs or releases magnetic material at the same timing respectively.

Furthermore, in the present invention, processing can be enhanced and various types of liquid each requiring a specific process can be processed by providing a plurality of liquid suction lines described above and controlling each of the liquid suction lines so that magnetic material is absorbed or released by sucking or discharging each liquid containing the magnetic material independently at a different timing according to a specified process required for each liquid.

The processing capability can be furthermore enhanced by integrating a liquid suction line and a magnet body into a unit and providing a plurality of units along the container transfer line.

In the present invention, when a liquid containing magnetic material is sucked or discharged, the magnet material is absorbed onto an internal surface of the pipette chip, so that the magnetic material can almost completely be captured, and the pipette chip can be transferred to the next reaction process or processing step with the magnetic material deposited on the internal surface thereof.

The pipette chip is repeatedly used only for the same specimen in a process in which a specimen is processed according to a specified inspection method, so that cross contamination can be prevented. If the liquid suction line is based on a nozzle system in which a pipette chip is not loaded or unloaded, it is possible to prevent cross contamination by cleaning an internal surface of the liquid suction line by means of sucking and discharging a liquid.

Furthermore, in the present invention, operations for separating magnetic material from a liquid containing the magnetic material therein, agitation and cleaning are executed by sucking and discharging the liquid with the cleaned liquid suction line described above once or more, so that the magnetic material can almost completely be captured. In addition, in the present invention, the operations of agitating and cleaning magnetic material are executed, as described above, in the side of a liquid suction line of a pipette device by sucking and discharging a liquid, so that the magnetic material can homogeneously be diffused in a liquid, and also the cleaning efficiency can be improved. In addition, although sucking and discharge of a liquid is executed between a liquid suction line and a container, the liquid containing magnetic material never splashes out. As a result, the operations of agitation and cleaning can be stabilized and precision in measurement does not become low due to contamination by the magnetic material containing liquid splashing out.

In the present invention, a quantity of liquid to be sucked can be controlled by the liquid suction line accurately, so that both qualitative and quantitative analysis of a target material contained in a liquid can be executed with high precision.

Furthermore, the method according to the present invention can be applied to various types of apparatus, and in this case a mechanism required for controlling magnetic material can substantially be simplified, and precision in measurement substantially improved and stabilized.

Although the invention has been described with respect to a specific embodiment for a complete and clear disclosure, the appended claims are not to be thus limited but are to be construed as embodying all modifications and alternative constructions that may occur to one skilled in the art which fairly fall within the basic teaching herein set forth.

What is claimed is:

1. A magnetic substance attracting/releasing control method comprises the steps of: providing a pipette device having a liquid suction line including a liquid inlet end for sucking a liquid containing said magnetic substance from a container and discharging said liquid through said liquid inlet end, and a magnet body or magnet bodies being detachably fitted to an external peripheral surface of said liquid suction line of said pipette device; said pipette device providing attracting/releasing control by absorbing and maintaining said magnetic substance contained in said liquid and attracted to said liquid suction line due to magnetism in said magnet body or bodies on an internal surface of said liquid suction line, said magnetic substance being maintained on said internal surface of said pipette device and also by releasing said magnetic substance from said liquid suction line by means of interrupting effect by magnetism in said magnet body or bodies so that said substance is discharged together with said liquid to outside of said liquid suction line through said liquid inlet end.

2. A magnetic material attracting/releasing control method which comprises using a pipette device according to claim 1, wherein a plurality of said liquid suction lines are provided in parallel to each other and operations of said liquid suction lines for sucking and discharging said liquid are driven and controlled so that said magnetic material is concurrently sucked and discharged at the same time respectively.

3. A magnetic material attracting/releasing control method which comprises using a pipette device according to claim 1, wherein a plurality of said liquid suction lines are provided parallel to to one another, and each of said liquid suction lines is driven and controlled so that a liquid in each liquid suction line is sucked and discharged independently at a different time and through a specific process to each liquid suction line respectively to attract or release magnetic material.

4. A magnetic material attracting/releasing control method which comprises using a pipette device according to claim 1, wherein said liquid suction line and magnetic body or bodies are integrated into a unit and a plurality of said units are provided along a container transfer line.

5. A magnetic material attracting/releasing control method which comprises using a pipette device according to claim 1, wherein at least one unit containing said magnet bodies is provided on said liquid suction line.

6. A magnetic material attracting/releasing control method which comprises using a pipette device according to claim 1, wherein said magnet body or bodies are provided outside said liquid suction line.

7. A magnetic material attracting/releasing control method which comprises using a pipette device according to claim 1, wherein said magnet body or bodies are mounted on said liquid suction line.

8. A magnetic material attracting/releasing control method which comprises using a pipette device according to claim 1, wherein said magnet body comprises a permanent magnet, said magnetic material contained in said liquid and attracted by said liquid suction line is absorbed to and deposited on said internal surface of said liquid suction line by getting said magnet body closer to said liquid suction line, and said magnetic material is discharged together with said liquid to outside said liquid suction line by separating said magnetic material from said liquid suction line by means of getting said magnet body away from said liquid suction line.

9. A magnetic material attracting/releasing control method which comprises using a pipette device according to claim 1, wherein said magnet body comprises an electromagnet, said magnetic material contained in a liquid and attracted by said liquid suction line is absorbed and maintained on said internal surface of said liquid suction line by generating a magnetic force with said electromagnet, and said magnetic material is separated from said liquid suction line and discharged together with a liquid from said liquid suction line when a magnetic force generated by said electromagnet is eliminated or fully reduced.

10. A magnetic material attracting/releasing control method which comprises using a pipette device according to claim 1, wherein a pipette tip is dismountably mounted onto a tip section of said liquid sucking side of said liquid suction line to form said liquid suction line, and a magnetic force generated by said magnet body provides an effect over magnetic material in a liquid stored in said pipette tip.

11. A magnetic material attracting/releasing control method which comprises using a pipette device according to claim 10, wherein said pipette tip is transferred to a specific processing position according to the particular inspection method used with magnetic material absorbed and maintained on said internal surface thereof.

12. A magnetic material attracting/releasing control method which comprises using a pipette device according to claim 10, wherein said pipette tip is repeatedly used only for a single specimen according to the specified inspection method required by said specimen.

13. A magnetic material attracting/releasing control method which comprises using a pipette device according to claim 10, wherein operations for separating said magnetic material from said liquid containing it therein, agitation and cleaning are executed after inside and outside of a liquid-contacting section of said liquid suction line by means of sucking and discharging said liquid repeatedly to a degree at which cross contamination does not occur.

14. A magnetic material attracting/releasing control method which comprises using a pipette device according to claim 1, wherein separation of said magnetic material from said liquid containing it therein, agitation, and cleaning operations are executed by conducting said operations for sucking and discharging said liquid with said liquid suction line once or more.

15. A magnetic material attracting/releasing control method which comprises using a pipette device according to claim 14, wherein said separation of magnet material from said liquid containing it therein is executed by discharging only said liquid with said magnetic material kept attracted by said magnet body.

16. A magnetic material attracting/releasing control method which comprises using a pipette device according to claim 14, wherein said agitation is executed, after a pipette tip has been inserted into a liquid stored in another container with magnetic material attracted on an internal surface of said pipette tip by said magnet body, by sucking and discharging said liquid repeatedly in a state where said operations are not affected by a magnet force generated by said magnet body.

17. A magnetic material attracting/releasing control method which comprises using a pipette device according to claim 14, wherein said cleaning operation is executed, after a pipette tip is transferred to a cleaning position with said magnetic material attracted onto an internal surface of said pipette tip by said magnet body, by sucking and discharging a cleaning liquid repeatedly.

18. A magnetic material attracting/releasing control method which comprises using a pipette device according to claim 14, wherein said cleaning operation with said cleaning liquid is executed with magnetic material attracted onto an internal surface of said pipette tip.

19. A magnetic material attracting/releasing control method which comprises using a pipette device according to claim 18, wherein said cleaning with said cleaning liquid is executed by sucking and discharging said cleaning liquid once or more in a stage where said cleaning operations are not affected by a magnetic force generated by said magnet body.

20. A magnetic material attracting/releasing control method which comprises using a pipette device according to claim 14, wherein said separation of magnetic material from a liquid containing it therein, agitation, and cleaning are executed by sucking and discharging a liquid previously stored in a liquid storage section provided in a cartridge with one or more liquid storage sections provided therein.

21. A magnetic material attracting/releasing control method which comprises using a pipette device according to claim 14, wherein said separation of magnetic material from a liquid in which it is contained, agitation, and cleaning are executed by discharging a residual liquid from said container to outside of said container with magnetic material deposited on an internal surface of a pipette tip then pouring a liquid required for a subsequent processing into the same container, and sucking and discharging the poured liquid with said pipette tip.

* * * * *